US 6,638,262 B2

(12) United States Patent
Suzuki et al.

(10) Patent No.: US 6,638,262 B2
(45) Date of Patent: Oct. 28, 2003

(54) DISPOSABLE WEARING ARTICLE

(75) Inventors: Seiji Suzuki, Kagawa-ken (JP); Takaaki Shimada, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/977,470

(22) Filed: Oct. 15, 2001

(65) Prior Publication Data

US 2002/0045876 A1 Apr. 18, 2002

(30) Foreign Application Priority Data

Oct. 16, 2000 (JP) ........................................ 2000-315703

(51) Int. Cl.$^7$ ............................................... A61F 13/15
(52) U.S. Cl. ........................... 604/385.28; 604/385.29; 604/385.101; 604/385.24
(58) Field of Search ........................ 604/385.28, 385.26, 604/385.01, 385.04, 385.29, 385.27, 385.25, 385.24, 385.3, 385.101

(56) References Cited

U.S. PATENT DOCUMENTS

| | | | | |
|---|---|---|---|---|
| 3,951,150 A | * | 4/1976 | Schaar | 604/389 |
| 5,026,364 A | * | 6/1991 | Robertson | 604/385.3 |
| 5,342,342 A | * | 8/1994 | Kitaoka | 604/385.2 |
| 5,576,091 A | * | 11/1996 | Zajaczkowski et al. | 428/192 |
| 5,649,918 A | * | 7/1997 | Schleinz | 604/385.26 |
| 5,904,675 A | | 5/1999 | Laux et al. | |
| 6,132,410 A | * | 10/2000 | Van Gompel et al. | 604/385.25 |
| 6,152,908 A | * | 11/2000 | Widlund et al. | 604/385.19 |
| 6,402,729 B1 | * | 6/2002 | Boberg et al. | 604/385.28 |
| 6,491,677 B1 | * | 12/2002 | Glaug et al. | 604/387 |

FOREIGN PATENT DOCUMENTS

| | | | |
|---|---|---|---|
| EP | 0 998891 A2 * | 5/2000 | A61F/13/15 |
| GB | 2 159 693 A | 12/1985 | |
| JP | 4-354948 | 12/1992 | |

* cited by examiner

Primary Examiner—Glenn K. Dawson
Assistant Examiner—Jacqueline F Stephens
(74) Attorney, Agent, or Firm—Butzel Long

(57) ABSTRACT

A disposable wearing article includes a substantially liquid-impervious leak-barrier cuff which has a fixed end portion lying in the vicinity of a longitudinal end portion of an article, a free end portion extending from the fixed end portion toward a crotch region and fixed lateral end portions lying on transversely opposite side edge portions of the article. The free end portion is normally biased to rise on a topsheet and locally bonded to the article in retaining zones.

5 Claims, 11 Drawing Sheets

DISPOSABLE WEARING ARTICLE

BACKGROUND OF THE INVENTION

This invention relates to a disposable wearing article such as a disposable diaper adapted to absorb and to contain excretion discharged thereon.

Japanese Patent Application Publication No. 1992-354948A describes a pants-type disposable diaper comprising a liquid-pervious topsheet, a liquid-impervious backsheet and a liquid-absorbent core disposed between the top- and backsheets, configuring a front waist region and a rear waist region opposed to each other and a crotch region extending between these waist regions so that the front and rear waist regions may be bonded together along side edge portions thereof to form the pants-type disposable diaper defining a waist-opening and a pair of leg-openings.

In the vicinity of a peripheral edge portion of the waist-opening, a substantially liquid-impervious leak-barrier cuff associated with the waist-opening extends in a waist-surrounding direction on the side of outer surface of the topsheet. The leak-barrier cuff has a first cuff extending in the waist-surrounding direction across the front waist region and a second cuff extending in the waist-surrounding direction across the rear waist region. The first cuff has a dimension approximately equal to one half of a wearer's waist size and the second cuff has a dimension approximately equal to the other half of the wearer's waist size.

The cuff comprising these two cuff-halves has a fixed end portion lying adjacent the peripheral edge portion of the waist-opening and bonded to the diaper, a free end portions extending from the fixed end portion toward the crotch region and fixed lateral end portions lying on the transversely opposite side edge portion of the front and rear waist regions and bonded to the diaper. The free end portion is provided with an elastic member being stretchable in the waist-surrounding direction and bonded under tension to the free end portion. The free end portion of the cuff is normally biased under contractile force of the elastic member to rise on the topsheet and thereby to form a barrier against excretion.

Of the leak-barrier cuff, the free end portion extending in the waist-surrounding direction between the fixed lateral end portions are not bonded to the diaper, so the free end portions may often be turned up as the diaper worn is vertically moved along the wearer's waist. Having been turned up, the leak-barrier cuff no more functions as the barrier against excretion and consequently excretion may leak out beyond the peripheral edge portions of the waist-opening.

SUMMARY OF THE INVENTION

It is an object of this invention to provide a disposable wearing article improved so that the free end portion of the leak-barrier cuff associated with the waist-opening is not easily turned up and reliably functions as the barrier against leak of excretion.

According to this invention, there is provided a disposable wearing article comprising a liquid-pervious topsheet, a liquid-impervious backsheet, a liquid-absorbent core, configuring a front waist region, a rear waist region and a crotch region extending between the front and rear waist regions, longitudinally opposite end portions extending in a first direction across the front and rear waist regions, respectively, transversely opposite side edge portions extending between the longitudinally opposite end portions in a second direction, and a substantially liquid-impervious leak-barrier cuff associated with a waist-opening lying on an outer surface of the topsheet and extending in the first direction across at least one of the front and rear waist regions.

The disposable wearing article further comprises the leak-barrier cuff which has a fixed end portion lying adjacent one longitudinal end portion of the article, a free end portion extending from the fixed end portion toward the crotch region and fixed lateral end portions lying on the side edge portions and bonded to the article wherein elastic member being stretchable in the first direction is attached under tension to the free end portion, normally biasing the free end portion to rise on the topsheet and the free end portion has at least one retaining zone in which the free end portion is bonded to the article.

According to one embodiment of this invention, the core has transversely opposite side edges extending in the second direction inside the fixed lateral end portions of the leak-barrier cuff and the retaining zone is defined between the fixed side portion of the cuff and adjacent the side edge of the core.

According to another embodiment of this invention, the free end portion defines a free edge extending in the first direction so as to describe a circular arc which is convex toward the longitudinal end portion of the article.

DETAILED DESCRIPTION OF THE PREFERRED EMBODIMENTS

Details of a disposable wearing article according to this invention will be more fully understood from the description of a pants-type diaper as one embodiment of this invention given hereunder with reference to the accompanying drawings.

Figure 1:
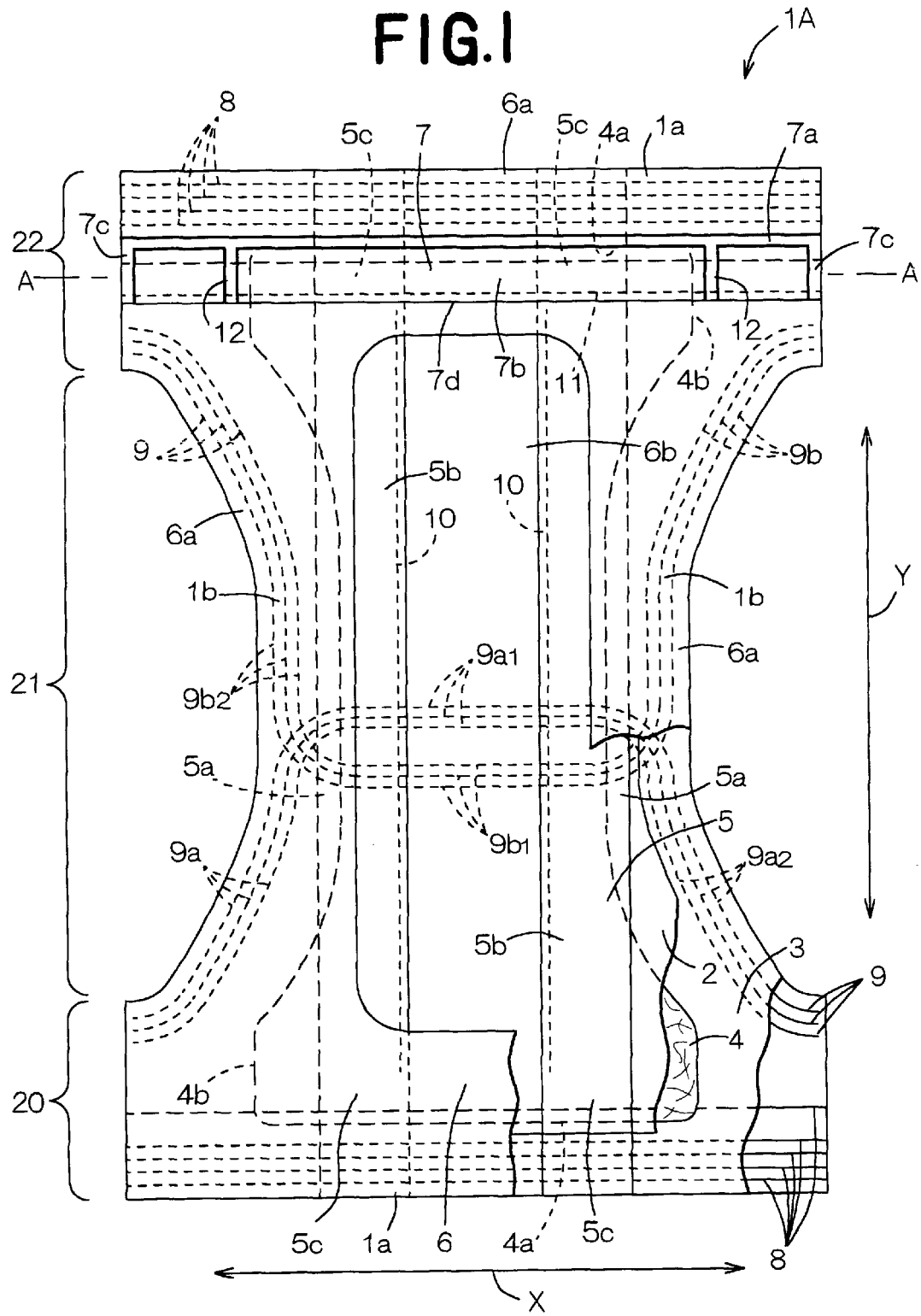
FIG. 1 is a plan view showing a diaper before shaped into a pants-type diaper as partially broken away.
Figure 2:
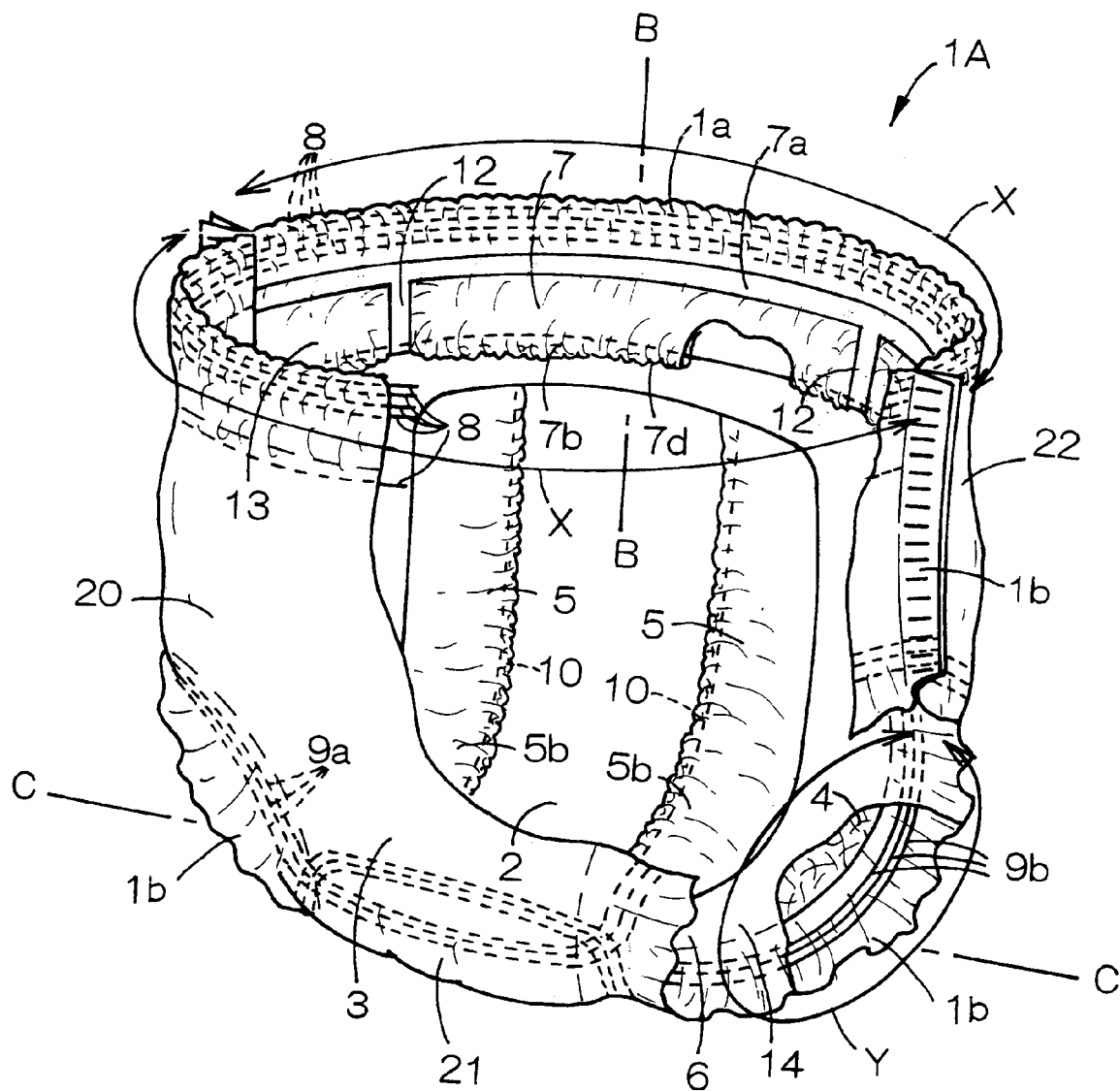
FIG. 2 is a perspective view showing the diaper shaped into the pants-type diaper from the state of FIG. 1 as partially broken away.

FIG. 1 is a plan view showing a diaper 1A before shaped into a pants-shape as partially broken away and FIG. 2 is a perspective view showing the diaper 1A having been shaped into such a pants-type diaper. Referring to FIG. 1, a transverse direction is indicated by an arrow X and a longitudinal direction is indicated by an arrow Y. Referring to FIG. 2, a waist-surrounding direction is indicated by an arrow X and a leg-surrounding direction is indicated by an arrow Y. The transverse direction as well as the waist-surrounding direction correspond to a first direction described in Claims and the longitudinal direction as well as the leg-surrounding direction correspond to a second direction described in Claims. The expression used herein "inner surfaces" of top- and backsheets 2, 3 and cover sheet 6 should be understood to be the surfaces thereof facing a liquid-absorbent core 4 and the expression used herein "outer surfaces" of these sheets 2, 3, 6 should be understood to be the surfaces thereof not facing the core 4.

The diaper 1A comprises the liquid-pervious topsheet 2, the liquid-impervious backsheet 3, the liquid-absorbent core 4 disposed between the top- and backsheets 2, 3 and entirely covered with and bonded to a liquid-dispersion sheet such as tissue paper (not shown), a pair of substantially liquid-impervious leak-barrier cuffs 5 associated with leg-openings, the cover sheet 6 being substantially liquid-impervious and having a central opening 6b of a substantially rectangular shape extending in the longitudinal direction and a substantially liquid-impervious leak-barrier cuff 7 associated with a waist-opening.

As seen in FIG. 1, the diaper 1A is composed, in the longitudinal direction, a front waist region 20, a rear waist region 22 and a crotch region 21 extending between these waist regions 20, 22, wherein the diaper 1A is contoured by longitudinally opposite end portions 1a extending in the transverse direction and transversely opposite side edge portions 1b extending in the longitudinal direction. In the crotch region 21, the side edge portions 1b curve inward in the transverse direction of the diaper 1A to describe circular arcs.

Elastic members 8 each comprising a plurality of elastic elements being stretchable in the transverse direction are attached under tension to the longitudinally opposite end portions 1a, respectively, so as to be associated with the waist-opening. In the crotch region 21, elastic members 9 each comprising a plurality of elastic elements being stretchable in the longitudinal direction are attached under tension to the transversely opposite side edge portions 1b so as to be associated with the respective leg-openings.

The core 4 has longitudinally opposite ends 4a extending in the transverse direction and transversely opposite side edges 4b extending in the longitudinal direction. The core 4 is bonded to inner surfaces of the top- and backsheets 2, 3, respectively, by means of the tissue paper.

The pair of the leak-barrier cuffs 5 associated with the leg-openings are attached to the respective side edge portions 1b of the diaper and extend in the longitudinal direction. The cover sheet 6 is attached to the outer surface of the topsheet 2. The leak-barrier cuff 7 associated with the waist-opening is attached to the outer surface of the cover sheet 6 in the rear waist region 22 and extends in the transverse direction.

The leak-barrier cuffs 5 have fixed side edge portions 5a extending in the longitudinal direction in the vicinity of transversely opposite side edges 4b of the core 4, free side edge portions 5b being contiguous to the respective fixed side edge portions 5a and fixed longitudinally opposite end portions 5c collapsed inward in the transverse direction of the diaper 1A and bonded to the topsheet 2 in such collapsed state. Elastic members 10 being stretchable in the longitudinal direction are attached under tension to the respective free side edge portions 5b and normally bias them to rise on the topsheet 2. These elastic members 10 are covered with parts of the respective free side edge portions 5b. The fixed side edge portions 5a are firmly bonded to the outer surface of the topsheet 2 in the vicinity of the respective side edges 4b of the core 4 (See FIG. 5). The fixed side edge portions 5c are firmly bonded to the outer surface of the topsheet 2 in the front and rear waist regions 20, 22.

The cover sheet 6 covers the end portions 1a as well as the side edge portions 1b of the diaper 1A and the fixed side edge portions 5a as well as the fixed end portions 5c of the leak-barrier cuffs 5. Specifically, the cover sheet 6 has its inner surface firmly bonded to the end portions 1a as well as the side edge portions 1b of the diaper 1A and additionally to the fixed side edge portions 5a as well as the fixed longitudinally opposite end portions 5c. The opening 6b of the cover sheet 6 extends across a substantially entire area of the crotch region 21 and further extends slightly into the front and rear waist regions 20, 22.

The leak-barrier cuff 7 has a fixed end portion 7a lying adjacent the end portion 1a of the rear waist region 22, a free end portion 7b extending the fixed end portion 7a toward the crotch region 21 and fixed lateral end portions 7c lying on the side edge portions 1b of the rear waist region 22 and extending in the longitudinal direction. The free end portion 7b has a free edge 7d extending in the transverse direction so as to define substantially straight line. An elastic member 11 being stretchable in the transverse direction is attached under tension to the free end portion 7b. The free end portion 7b is normally biased by contraction of the elastic member 11 to rise on the topsheet 2 so that an intermediate portion of the free end portion 7b can extend upward. The elastic member 11 is covered with a part of the free end portion 7b. The fixed end portion 7a and the fixed longitudinally opposite end portions 7c are firmly bonded to the outer surface of the cover sheet 6.

The free end portion 7b includes a pair of retaining zones 12 vertically extending immediately outside the transversely opposite side edges 4b of the core 4. The free end portion 7b is bonded to the outer surface of the cover sheet 6 in the retaining zones 12. In the leak-barrier cuff 7, movement of the free end portion 7b is constrained by the retaining zones 12 and the free end portion 7b is not so easily turned up as the case in which the free end portion 7b is bonded to the cover sheet 6 only at the side portions 7c.

Elastic member 9 associated with the leg-openings comprises a first elastic member 9a and a second elastic member 9b. These elastic members 9a, 9b associated with the leg-openings have intermediate sections 9a1, 9b1 extending across the crotch region 21 and remaining sections 9a2, 9b2 extending along the transversely opposite side edge portions 1b of the diaper 1A. The remaining sections 9a2 of the first elastic member 9a extend along substantially front halves of the transversely opposite side edge portions 1b of the crotch region 21 and the remaining sections 9b2 of the second elastic member 9b extend along substantially rear halves of the transversely opposite side edge portions 1b of the crotch region 21.

The diaper 1A may be shaped from the state shown in FIG. 1 into the pants-shape shown in FIG. 2 by bonding the front and rear waist regions 20, 22 to each other intermittently along the transversely opposite side edge portions 1b thereof. With the diaper 1A shaped into the pants-shape in this manner, a waist-opening 13 and a pair of leg-openings 14 are defined.

Of the diaper 1A, the longitudinally opposite end portions 1a define the peripheral edge portion of the waist-opening 13 and the transversely opposite side edge portions 1b in the crotch region 21 define peripheral edge portions of the respective leg-openings 14. The elastic members 8 associated with the waist-opening extend along the peripheral edge portion 1a of the waist-opening 13 in the waist-surrounding direction. The elastic members 9 associated with the leg-openings extend along the peripheral edge portions 1b of the respective leg-openings 14 in the leg-surrounding direction. Of the diaper 1A, the leak-barrier cuffs 5 extend along the peripheral edge potions 1b of the respective leg-openings 14 and the leak-barrier cuff 7 extends along the peripheral edge portion 1a of the waist-opening 13 in the rear waist region 22.

In the diaper 1A, contraction of the elastic members 8, 9 causes the peripheral edge portion 1a of the waist-opening 13 as well as the peripheral edge portions 1b of the respective leg-openings 14 to form a plurality of gathers. Contraction of the elastic members 10 causes the free side edge portions 5b of the respective leak-barrier cuffs 5 to rise on the topsheet 2 and contraction of the elastic member 11 causes the free end portion 7b of the leak-barrier cuff 7 to rise on the cover sheet 6.

Figure 3:
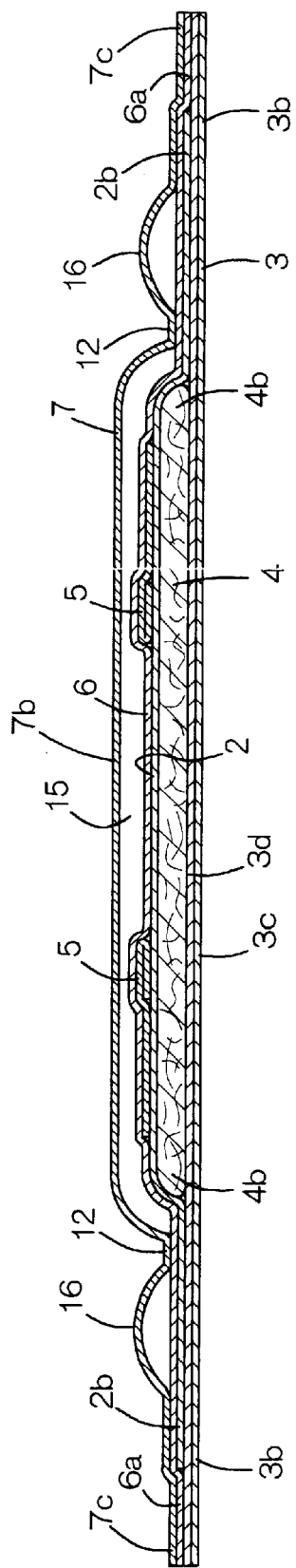
FIG. 3 is a sectional view taken along a line A—A in FIG. 1.
Figure 4:
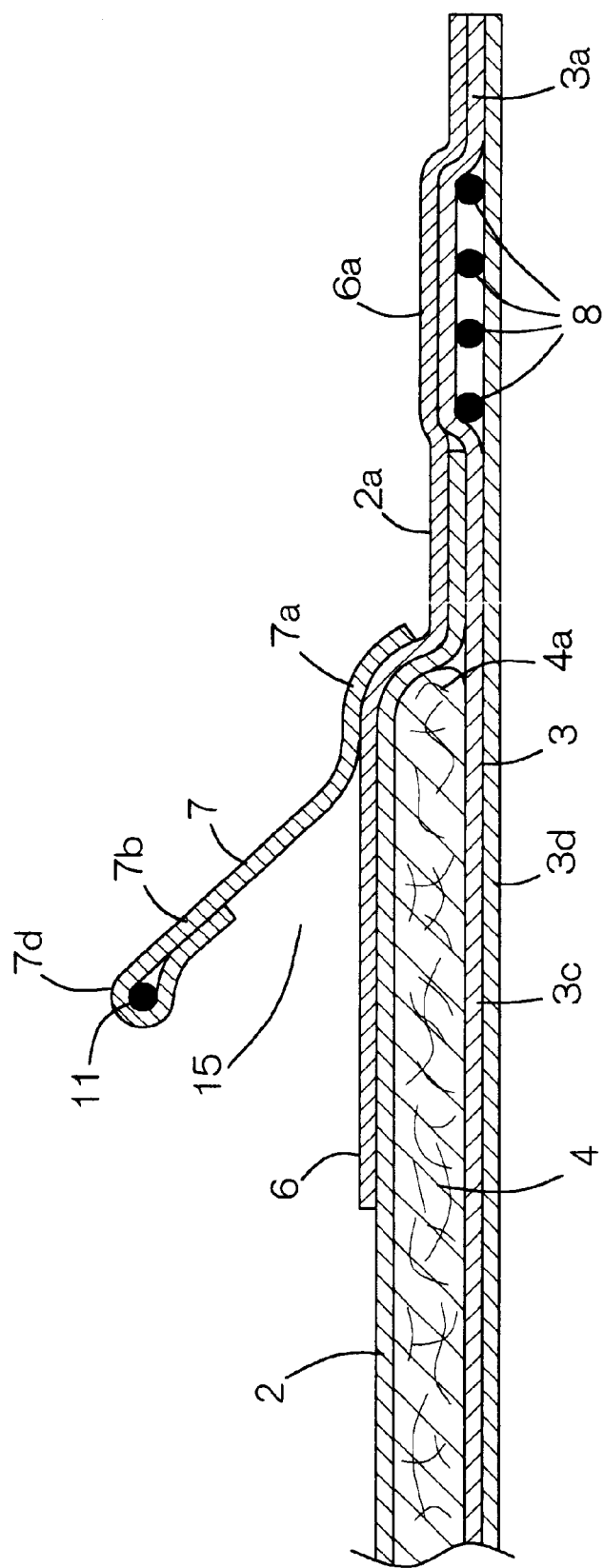
FIG. 4 is a sectional view taken along a line B—B in FIG. 2.
Figure 5:
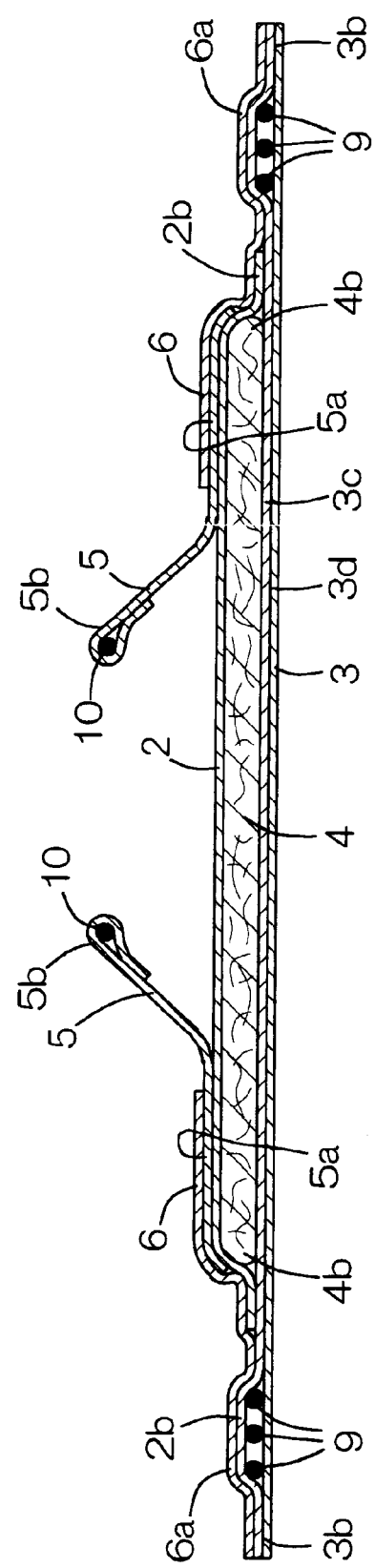
FIG. 5 is a sectional view taken along a line C—C in FIG. 2.

FIG. 3 is a sectional view taken along a line A—A in FIG. 1, FIG. 4 is a sectional view taken along a line B—B in FIG. 2 and FIG. 5 is a sectional view taken along a line C—C in FIG. 2. In the rear waist region 22, a portion of the free end portion 7b of the leak-barrier cuff 7 extending between the retaining zones 12 cooperates with the cover sheet 6 to form a space 15 adapted to receive excretion. Portions of the free end portion 7b of the leak-barrier cuff 7 extending between the retaining zones 12 and the adjacent fixed lateral end portions 7c cooperate with the cover sheet 6 to form a space 16 adapted to receive excretion.

In the rear waist region 22, the free end portion 7b of the leak-barrier cuff 7 rises to form the barrier against excretion and thereby prevents excretion leak from occurring in the vicinity of the longitudinal end portion 1a in the rear waist region 22. Of the leak-barrier cuff 7, the retaining zones 12 extend immediately outside the respective side edges 4b of the core 4, so the core 4 is not covered with the free end portion 7b. In other words, the free end portion 7b can rise without any obstruction and dams up the amount of excretion having reached the longitudinal end 4a of the core 4. It should be understood that of the leak-barrier 7, a pair of the retaining zones 12 may extend immediately inside the side edges 4b of the core 4 or the single retaining zone 12 may vertically extend in the transversely middle of the core 4.

As will be seen in FIG. 4, in the vicinity of the peripheral edge portion 1a of the waist-opening 13, the longitudinal end portion 2a of the topsheet 2 extends outward slightly beyond the longitudinal end 4a of the core 4. The longitudinal end portion 3a of the backsheet 3 and a peripheral edge portion 6a of the cover sheet 6 extends further outward beyond the longitudinal end portion 2a of the topsheet 2. The end portion 2a is disposed between the longitudinal end portion 3a and the peripheral edge portion 6a and bonded to these end portion 3a and peripheral edge portion 6a. The longitudinal end portion 3a is bonded to the peripheral edge portion 6a along a zone in which these two portions 3a, 6a are placed upon each other. The longitudinal end portion 2a of the topsheet 2 terminates at a level lower than the longitudinal edge portion 1a of the diaper and therefore it is not apprehended that the amount of excretion having reached the longitudinal end portion 2a might leak out from the longitudinal end portion 1a.

The backsheet 3 is formed with a composite sheet made of plastic film 3c and hydrophobic fibrous nonwoven fabric 3d laminated with the film 3c with the elastic member 8 associated with the waist-opening disposed between these plastic film 3c and nonwoven fabric 3d.

As will be seen in FIG. 5, in the vicinity of the peripheral edge portions 1b of the respective leg-openings 14, transversely opposite side edge portions 2b of the topsheet 2 extend outward slightly beyond the respective side edges 4b of the core 4 and transversely opposite side edge portions 3b of the backsheet 3 as well as the peripheral edge portion 6a of the cover sheet 6 extend further outward beyond the side edge portions 2b of the topsheet 2. The side edge portions 2b are disposed between and bonded to the side edge portions 3b and the peripheral edge portion 6a. The side edge portions 3b and the peripheral edge portion 6a are bonded to together in a zone along which these two portions 3b, 6a are placed upon each other. The respective elastic members 9 associated with the leg-openings are disposed and bonded between the plastic film 3c and the hydrophobic nonwoven fabric 3d forming the backsheet 3.

In the crotch region 21, the free side edge portions 5b of the respective leak-barrier cuffs 5 rise to form barriers adapted to avoid an anxiety that any amount of excretion might leak from the crotch region 21. In the vicinity of the peripheral edge portions 1b of the respective leg-openings 15, the transversely opposite side edge portions 2b of the topsheet 2 do not extend to the outermost edges of the respective peripheral edge portions 1b so that an amount of excretion having reached the transversely opposite side edge portions 2b can no more flow beyond the peripheral edge portions 1b.

Figure 6:
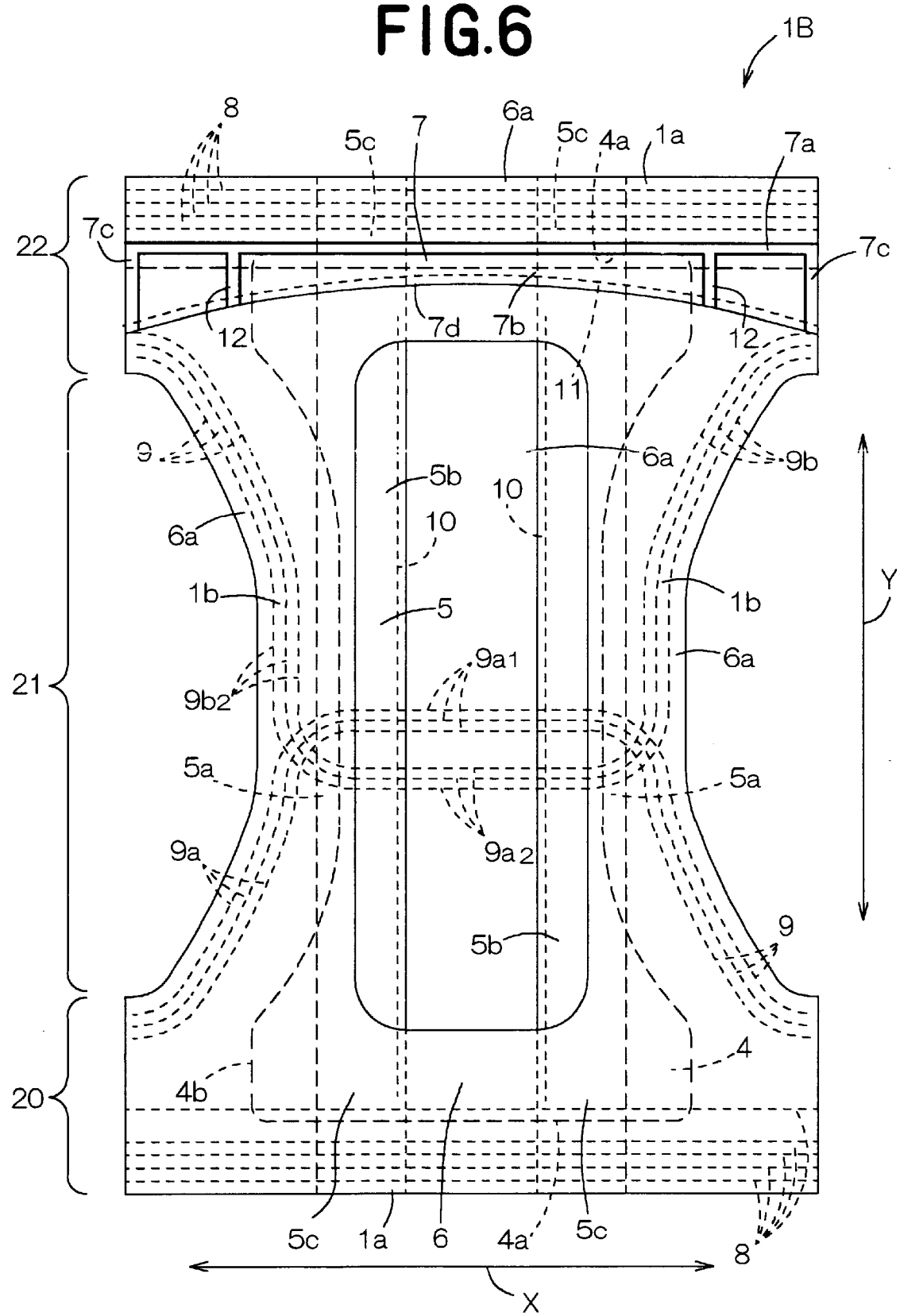
FIG. 6 is a plan view showing another embodiment of the diaper according to this invention.
Figure 7:
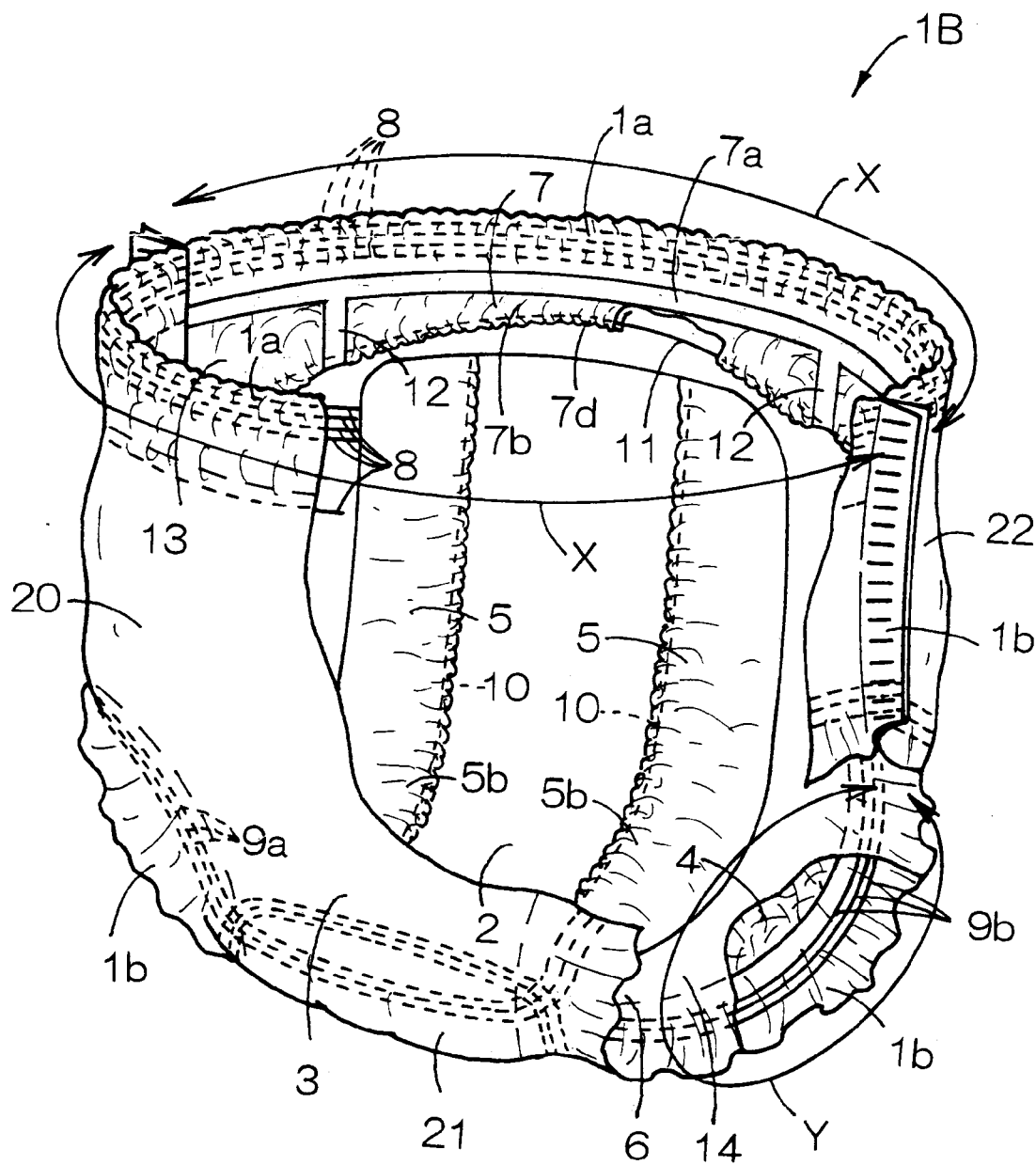
FIG. 7 is a perspective view showing the pants-type diaper obtained from the state shown in FIG. 6 as partially broken away.

FIG. 6 is a plan view showing the diaper 1B according to another embodiment of this invention and FIG. 7 is a perspective view showing this diaper 1B shaped into pants-type diaper as partially broken away. This diaper 1B is similar to the diaper 1A of FIG. 2 in that this diaper 1B comprises the liquid-pervious topsheet 2, the liquid-impervious backsheet 3, the liquid-absorbent core 4 disposed between the top- and backsheets 2, 3, the pair of substantially liquid-impervious leak-barrier cuffs 5 associated with leg-openings, the cover sheet 6 being substantially liquid-impervious and the leak-barrier cuff 7 associated with a waist-opening. The diaper 1B of FIG. 6 is different from the diaper 1A of FIG. 2 in features as will be described.

In the leak-barrier cuff 7, the free end portion 7b has a free edge 7d extending in the rear waist region 22 so as to describe a circular arc which is convex toward the peripheral edge portion 1a of the waist-opening 13. The free end portion 7b is provided along the free edge 7d with the elastic member 11 bonded under tension thereto. With this diaper 1B, the free edge 7d of the free end portion 7b extends along the wearer's hip as the diaper 1B is worn and there is no anxiety that the vicinity of the free edge 7d might be folded or the free end portion 7b might be turn up even if the free edge 7d comes in contact with the wearer's skin. Furthermore, the free end portion 7b of this diaper 1B is bonded to the cover sheet 6 in the retaining zones 12, so the free end portion 7b is not easily turned up as in the case of the diaper 1A of FIG. 1.

Figure 8:
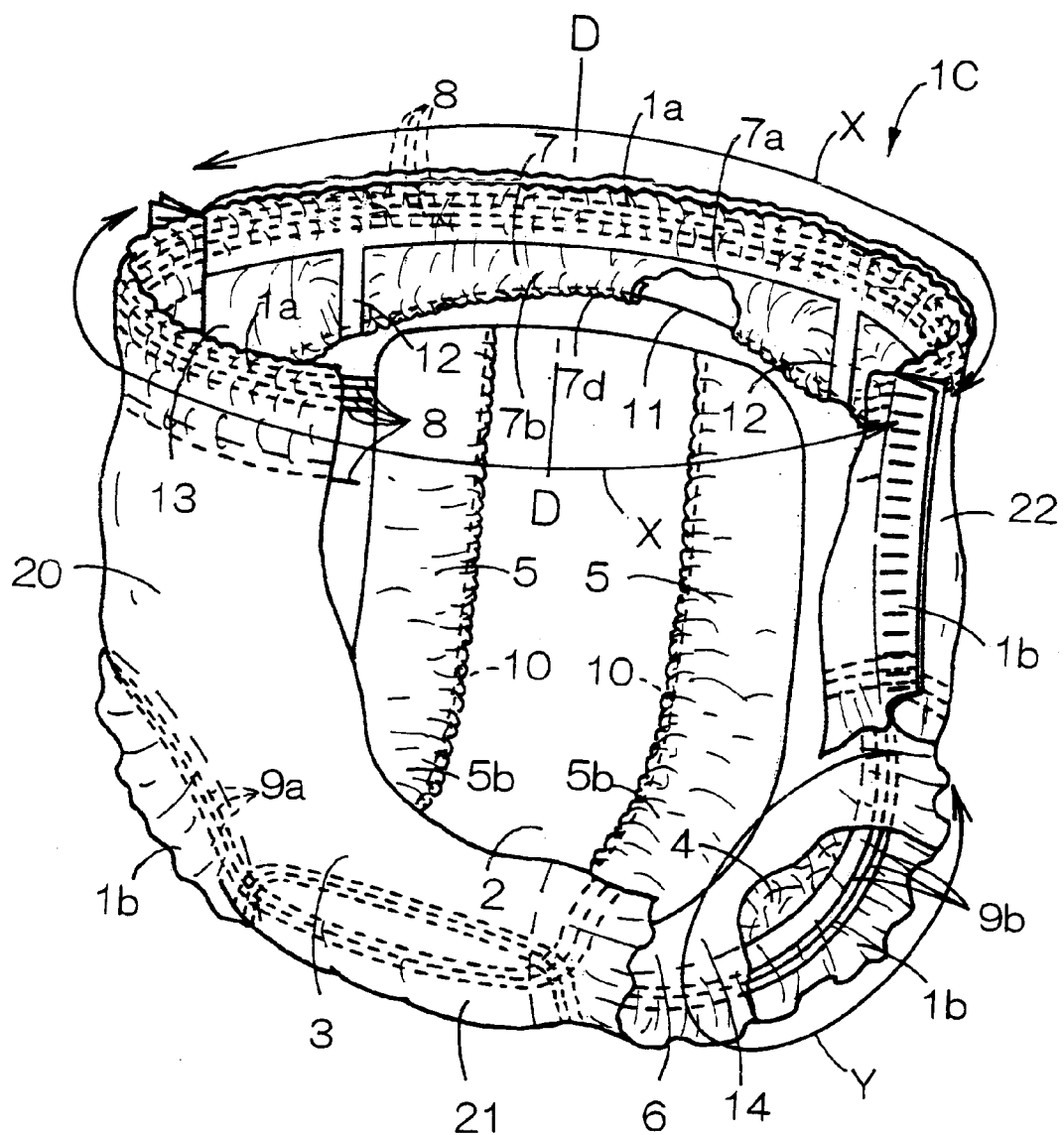
FIG. 8 is a perspective view showing still another embodiment of the pants-type diaper as partially broken away.
Figure 9:
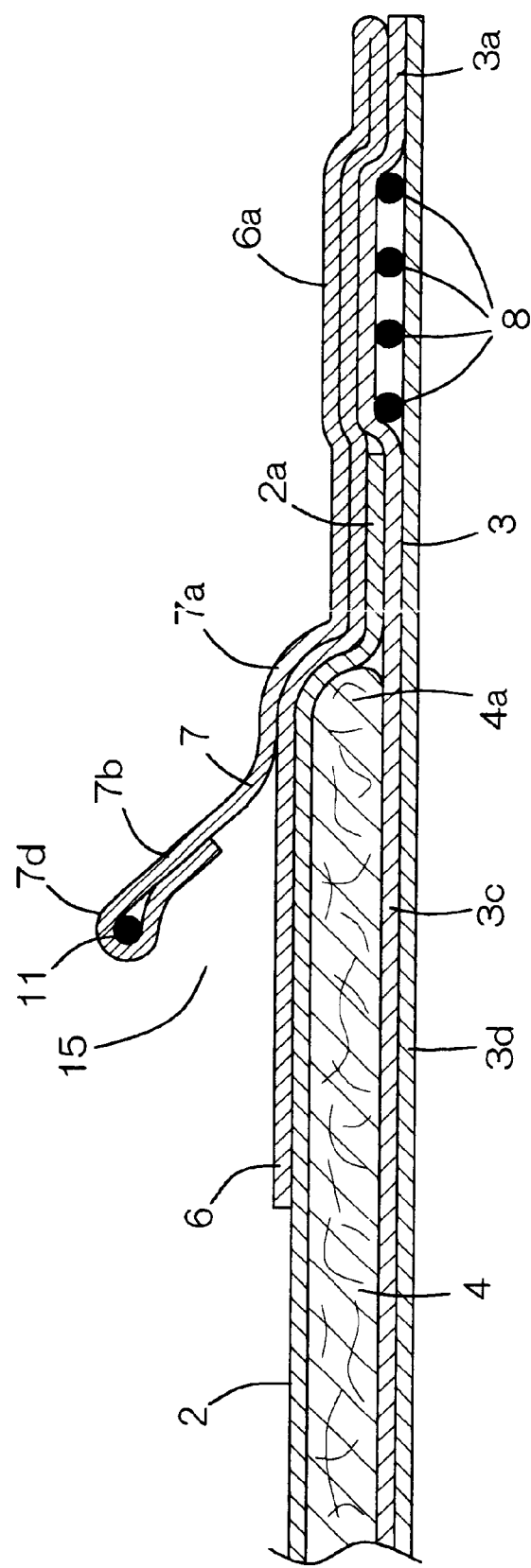
FIG. 9 is a sectional view taken along a line D—D in FIG. 8.

FIG. 8 is a perspective view showing a pants-type diaper 1C as still another embodiment as partially broken away and FIG. 9 is a sectional view taken along a line D—D in FIG. 8. In this diaper 1C, a part of the cover sheet 6 serves also as the leak-barrier cuff 7 associated with the waist-opening. This leak-barrier cuff 7 is defined by the part of the cover sheet 6 extending outward from the peripheral edge portion 1a of the waist-opening 13 in the rear waist region 22 and folded back along the peripheral edge portion 1a onto the outer surface of the cover sheet 6.

Figure 10:
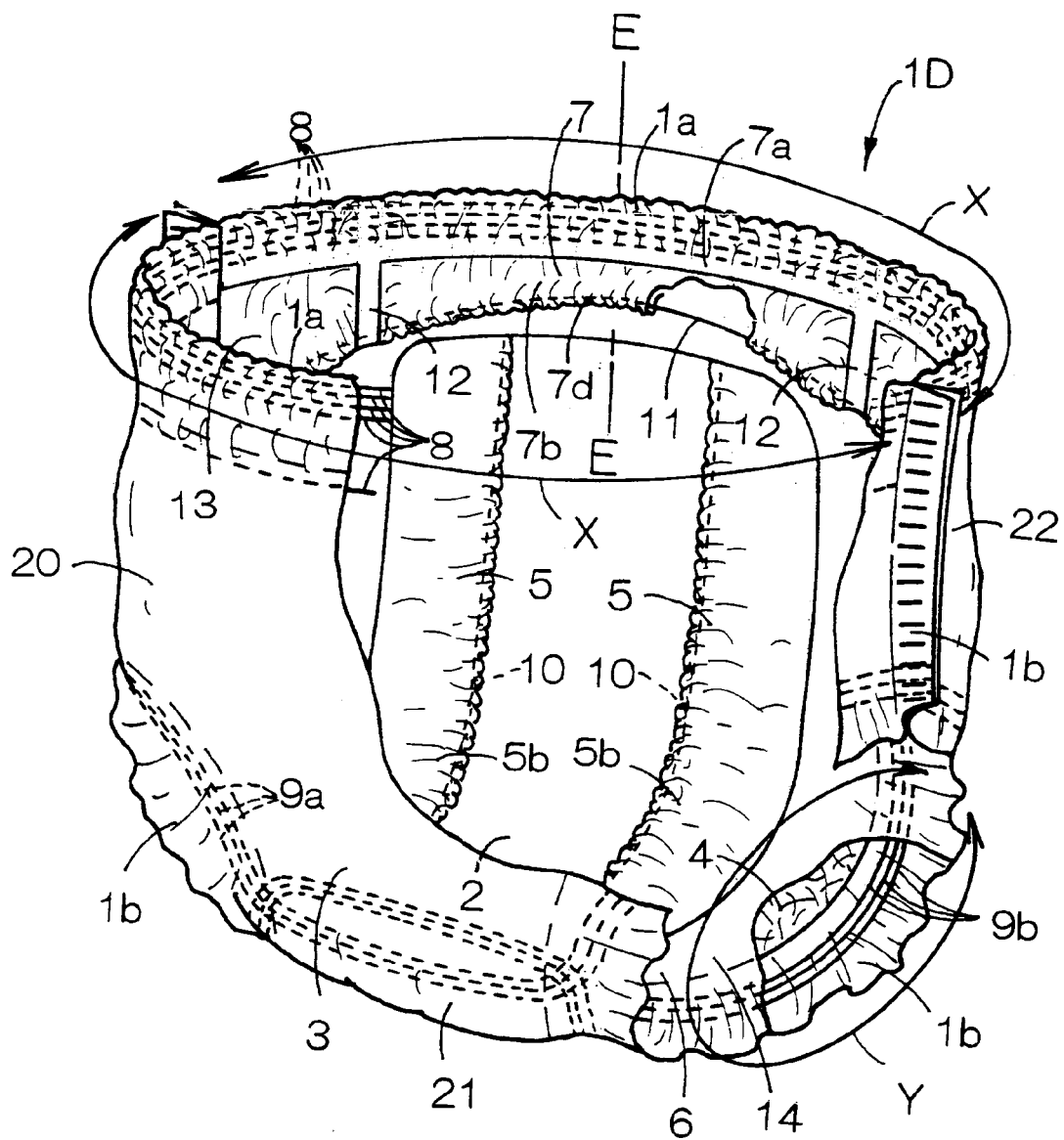
FIG. 10 is a perspective view showing further another embodiment of the pants-type diaper as partially broken away.
Figure 11:
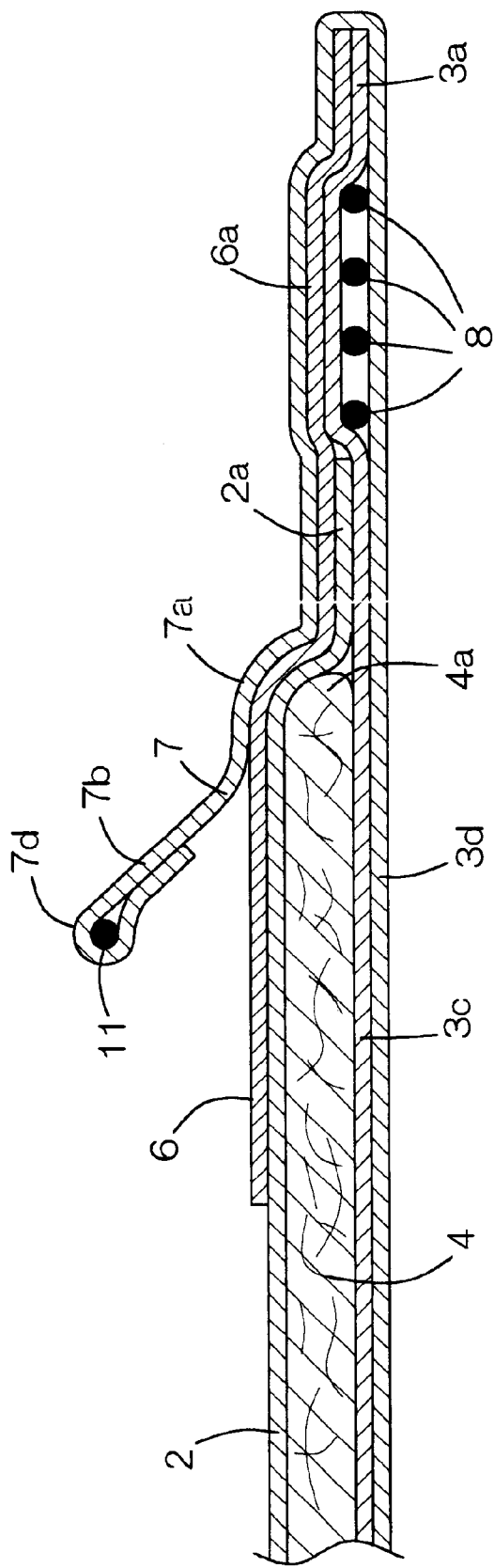
FIG. 11 is a sectional view taken along a line E—E in FIG. 10.

FIG. 10 is a perspective view showing a pants-type diaper 1D as still another embodiment as partially broken away and FIG. 11 is a sectional view taken along a line E—E in FIG. 10. In this diaper 1D, a part of the hydrophobic nonwoven fabric 3d forming the backsheet 3 serves also as the leak-barrier cuff 7 associated with the waist-opening. This leak-barrier cuff 7 is defined by the part of the hydrophobic nonwoven fabric 3d extending outward from the peripheral edge portion 1a of the waist-opening 13 in the rear waist region 22 and folded back along the peripheral edge portion 1a onto the outer surface of the cover sheet 6.

The diapers 1C shown by FIG. 8 is similar to the diaper 1D shown by FIG. 10 in that the fixed end portion 7a as well as the fixed lateral end portions 7c of the leak-barrier cuff 7 are bonded to the outer surface of the cover sheet 6 and the free end portion 7b of the leak-barrier cuff 7 is bonded to the outer surface of the cover sheet 6 in the retaining zones 12 extending immediately outside the transversely opposite side edges 4b of the core 4. These diapers 1C, 1D are similar to each other also in that the free edge 7d of the free end portion 7b extends so as to describe the circular arc which is convex toward the peripheral edge portion 1a of the waist-opening 13.

While the leak-barrier cuff 7 is provided in the rear waist region 22 in the diapers 1A~1D illustrated as the preferred embodiments of this invention, this leak-barrier cuff 7 may be provided not only in the rear waist region 22 but also in the front waist region 20 or only in the front waist region 20.

The topsheet 2 may be formed with a liquid-pervious sheet such as a nonwoven fabric or porous plastic film. The backsheet 3 may be formed with a laminated composite sheet of hydrophobic nonwoven fabric and plastic film, or hydrophobic nonwoven fabric, or liquid-impervious plastic film. The leak-barrier cuffs 5, the cover sheet 6 and the leak-barrier cuff 8 may be formed with composite nonwoven fabric consisting of melt blown nonwoven fabric having a high water-resistance and two layers of spun bond nonwoven fabric having high strength and flexibility sandwiching the melt blown nonwoven fabric.

The nonwoven fabric may be selected from a group including spun lace-, needle punch-, melt blown-, thermal bond-, spun bond-, chemical bond- and air through-nonwoven fabric. Component fiber of the nonwoven fabric may be selected from a group including polyolefine-, polyester- and polyamide-based fibers and polyethylene/polypropylene or polyethylene/polyester core-sheath type conjugated fiber and side-by-side-type conjugated fiber.

The core 4 is a mixture of fluff pulp, high absorption polymer grains and thermoplastic synthetic resin fiber compressed to a desired thickness. Therefore, the core 4 has a stiffness higher than those of the top- and backsheets 2, 3 and the cover sheet 6. The polymer grains may be selected from a group including starch-, cellulose-based polymer and synthetic polymer.

To bond the top- and backsheets 2, 3 to each other, to bond the leak-barrier cuffs 5, the cover sheet 6 and the leak-barrier 7 to the top- and backsheets 2, 3 and to bond the core 4 to the top- and backsheets 2, 3 and to attach the elastic members 8, 9, 10, 11, to the diaper, suitable adhesive such as hot melt adhesive or welding means such as heat-sealing or ultrasonic sealing may be used.

This invention may be also implemented in the form of an open-type diaper having its front and rear waist regions connected to each other through engagement between tape fasteners and a target tape strip.

In the disposable wearing article of this invention, the leak-barrier cuff associated with the waist-opening has its free end portion locally bonded to the article, i.e., in the retaining zones provided in the free end portion so that movement thereof may be appropriately constrained by the retaining zones. With such unique arrangement, the free end portion is not easily turned up even when the article put on the wearer's body moves in vertical direction around the wearer's waist. This free end portion of the leak-barrier cuff rises to from the barrier against excretion and reliably prevent excretion leak from occurring in the vicinity of the longitudinal end portion of the article.

In the case of the article implemented in the manner that the retaining zones are provided between the fixed lateral end portions and the transversely opposite side edges of the core, there is no anxiety that the free end portion might cover the longitudinal end of the core. In other words, the free end portion reliably rises on the cover sheet in the vicinity of the longitudinal end of the core and dams up the amount of excretion having reached the longitudinal end of the core.

In the case of the article implemented in the manner that the free end portion has its free edge curving so as to describe a circular arc which is convex toward the longitudinal end of the article, the free edge of the free end portion extends along the wearer's hip as the article is worn and there is no anxiety that the vicinity of the free edge might be folded or the free end portion might be turn up even if the free edge comes in contact with the wearer's skin.

What is claimed is:

1. A disposable wearing article comprising:

a liquid-pervious topsheet;

a liquid-impervious backsheet;

a liquid-absorbent core;

a front waist region;

a rear waist region;

a crotch region extending between said front and rear waist regions;

a waist opening;

a waistband including at least one elastic element that extends in a waist-surrounding direction, a pair of leg-openings;

longitudinally opposite end portions extending in a first direction across said front and rear waist regions, respectively, said first direction extending transversely of said disposable wearing article;

transversely opposite side edge portions extending between said longitudinally opposite end portions in a second direction, said second direction extending longitudinally of said disposable wearing article; and a substantially liquid-impervious leak-barrier cuff laying on an outer surface of said topsheet and extending in said first direction across at least one of said front and rear waist regions, said leak-barrier cuff having a fixed edge portion lying adjacent and spaced apart from one longitudinal end portion of said article with the waistband positioned between the fixed edge and the one longitudinal end portion of said article, a free edge portion extending from said fixed edge portion toward the crotch region, and fixed lateral end portions lying on respective ones of said side edge portions and bonded to said article wherein an elastic member being stretchable in said first direction is attached under tension to said free edge portion, normally biasing said free edge portion to rise on said topsheet and said free edge portion has at least one retaining zone in which said free edge portion is bonded to said article.

2. The article according to claim 1, wherein said core has transversely opposite side edges extending in said second direction inside said fixed lateral end portions of said cuff and said retaining zone is defined between the fixed side portion of said cuff and the adjacent the side edge of said core.

3. The article according to claim 1, wherein said free end portion defines a free edge extending in said first direction so as to describe a circular arc which is convex toward the longitudinal end portion of said article.

4. The article according to claim 1, wherein the fixed edge and the free edge of the leak-barrier cuff are substantially parallel to one another.

5. The article according to claim 1, wherein the fixed edge of the leak-barrier cuff extends substantially linearly in the first direction.

* * * * *